United States Patent [19]

Gandolfi et al.

[11] Patent Number: 5,162,320

[45] Date of Patent: Nov. 10, 1992

[54] 1,4-BIS(ALKYLAMINO)-2,3-DIAZA-ANTHRACENE-9,10-DIONES

[75] Inventors: Carmelo A. Gandolfi; Francis Johnson; Ernesto Menta; Silvano Spinelli; Sergio Tognella, all of Milan, Italy

[73] Assignee: Boehringer Biochemia Robin S.p.A., Milan, Italy

[21] Appl. No.: 602,526

[22] Filed: Oct. 25, 1990

[30] Foreign Application Priority Data

Oct. 27, 1989 [IT] Italy ................. 22175 A/89

[51] Int. Cl.⁵ ................. A61K 31/495; C07D 237/26; C07D 403/12; C07D 413/12
[52] U.S. Cl. ................. 514/248; 514/232.5; 514/232.8; 544/115; 544/234
[58] Field of Search ............... 544/234, 119, 234, 115; 514/248, 233.8, 232.5, 232.8

[56] References Cited

U.S. PATENT DOCUMENTS

| | | | |
|---|---|---|---|
| 3,497,512 | 2/1970 | Hofer et al. | 544/234 |
| 3,880,881 | 4/1975 | Singh | 544/234 |
| 4,275,009 | 6/1981 | Murdock | 552/247 |
| 4,278,605 | 7/1981 | Murdock | 552/218 |
| 4,428,882 | 1/1984 | Murdock | 552/247 |

*Primary Examiner*—Mukund J. Shah
*Assistant Examiner*—E. Bernhardt
*Attorney, Agent, or Firm*—Nikaido, Marmelstein, Murray & Oram

[57] ABSTRACT

Compounds of formula I are described,

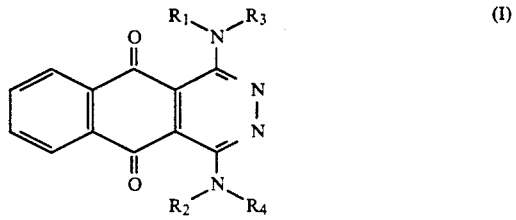

wherein:
$R_1$ and $R_2$, that can be the same or different, are hydrogen or acyl groups;
$R_3$ and $R_4$, that can be the same or different, are hydrogen or optionally substituted alkyl groups.

The compounds of formula I are prepared by oxydation of the compounds of formula II:

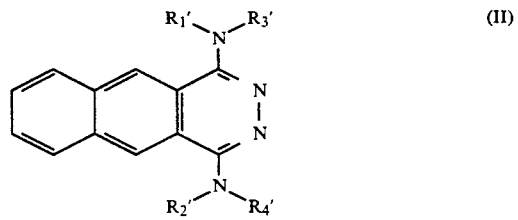

wherein the groups $R'_1$, $R'_2$, $R'_3$ and $R'_4$ have the same meanings as $R_1$, $R_2$, $R_3$ and $R_4$ or groups convertible to the latter.

The compounds of formula I have remarkable antitumor activity.

7 Claims, No Drawings

1,4-BIS(ALKYLAMINO)-2,3-DIAZA-ANTHRACENE-9,10-DIONES

The present invention relates to 1,4-bis(alkylamino)-2,3-diaza-anthracene-9,10-diones, to a method for their preparation and to pharmaceutical compositions containing them.

Chemotherapy proved to be promising in the treatment of many types of cancerous conditions. However, the major problem with nearly all conventional chemotherapeutic agents is their narrow therapeutic index. In addition, many antineoplastic agents are not devoid of serious or fatal toxic side effects. Therefore, further development of antitumor agents is of current interest. Although the anthracycline antibiotic doxorubicin has an established place in the treatment of various solid and hematological neoplasms, one major drawback is its severe dose-related cardiotoxicity. Numerous analogues of doxorubicin have been prepared in an effort to separate the antitumor and cardiotoxic effects, and some differences in antitumor activity and cardiotoxicity have been noted among these analogues (B. I. Sikic, Science, 228, 1544, (1985)).

Recently, synthesis and antineoplastic evaluation of a number of symmetrically substituted 1,4-bis[(aminoalkyl)amino]anthracene-9,10-diones have afforded a new class of chemotherapeutic agents among which ametantrone (1,4-bis[(2-(2-hydroxyethylamino)ethyl)amino]anthracene-9,10-dione) and mitoxantrone (5,8-dihydroxy-1,4-bis[(2-(2-hydroxyethylamino)ethyl)amino]anthracene-9,10-dione) are representative examples (R. K. Y. Zee-Cheng et al. J. Med Chem. (1978), 21, 291-294; K. C. Murdock et al, J. Med. Chem. (1979), 22, 1024-1030).

Both amentantrone and mitoxantrone showed outstanding antineoplastic activities.

Phase I and Phase II clinical trials evidenced the effectiveness of mitoxantrone in the treatment of various cancerous conditions such as advanced breast cancer, acute leukemias and certain lymphomas (S. S. Legha, Drugs of Today, (1984), 20, 629).

While the response rate of mitoxantrone is similar to that of doxorubicin, its toxic side effects are by far lower than those resulting from doxorubicin, which are nausea, vomiting and alopecia.

The major hematological toxicities associated with mitoxantrone treatment are leukopenia, neutropenia and bone marrow aplasia.

Although early studies indicated that mitoxantrone was less cardiotoxic than doxorubicin, some clinical cardiotoxicity with mitoxantrone has been reported, mostly in patients treated earlier with doxorubicin (R. Stuart-Harris et al., Lancet (1984), 219).

Moreover, a delayed lethality (not observed with ametantrone) was observed when mitoxantrone was administered intraperitoneally to non-tumor bearing animals (T. H. Corbet et al., Cancer Chemother. Pharmacol., (1981), 6, 161).

In conclusion, ametantrone and mitoxantrone can be regarded as simplified synthetic analogues of the anthracycline antibiotics of which they retain both some structural features (i.e. the planar anthraquinone moiety and a basic side chain) and some cardiotoxicity.

Easy synthesis and significant anticancer activity of said anthracenediones prompted the search for novel analogues endowed with a broader spectrum of activity and a more favourable therapeutic index.

To date primary structural changes have been variations in the side chains and the introduction of hydroxy substituents and/or of the (aminoalkyl)amino side chains in different positions of the anthraquinone system (L. C. Cheng et al., Drugs of the Future, (1983), 8, 229; L. C. Cheng, Progress in Medicinal Chemistry, Ed. G. P. Ellis and G. B. West, Elsevier 20, 83 (1983)).

The structure of the basic side chain seems to be able to modulate the antitumor properties of these substances. A great effort has been made in the synthesis of symmetrical and unsymmetrical analogues and also of derivatives wherein one of the two side chains is substituted by other groups such as amino or hydroxy.

Active analogues containing two anthraquinone units and (aminoalkyl)amino unsymmetrical 1,4-disubstitution have also been described (K. C. Murdock, U.S. Pat. No. 4,278,605, C. A. (1981), 95, 168877Y).

"Unsymmetrical" analogues of ametantrone and mitoxantrone with an (aminoalkyl)amino chain at position 1 and hydroxy or amino groups at position 4 have been described (R. K. Y. Zee Cheng, J. Med. Chem. (1979), 22, 501; C. C. Cheng and R. K. Y. Zee Cheng, U.S. patent application Ser. No. 142,745; K. C. Murdock, U.S. Pat. No. 4,428,882; K. C. Murdock, U.S. Pat. No. 4,275,009) and are referred to possess high antitumor activity in mice.

More recently, high antitumor activities in "in vitro" tests, that were not confirmed by subsequent studies in "in vivo" models, have been reported for some "unsymmetrical" analogues of ametantrone with different (aminoalkyl)amino chains at positions 1 and 4 (A. P. Krapcho et al., J. Med. Chem., (1986), 29, 1370).

The presence in these substances of an integral anthraquinone system does not seem to be an essential prerequisite for obtaining good antitumor activity. Some anthraiminoquinones such as alkylaminoanthra[1,9-c,d]pyrazole-6-(2 H)-ones and related benzothiopyrano[4,3,2-c,d]indazoles were disclosed by H. D. Showalter et al., (J. Med. Chem., (1987), 30, 121 and ibidem, (1988), 31, 1527.

It is noteworthy that, in the benzothiopyrane series, the carbonyl group of the anthrapyrazole-iminoquinone system is replaced more properly by a sulfur atom than by a closely mimic sulphoxide group; surprisingly this latter substitution gives rise to poorly active or inactive substances.

Little is known about other heterocyclic analogues of said antitumor anthracene-9,10-diones excepting for some mono-aza-anthraquinones wherein a methine ($>$C—H) is replaced by a nitrogen atom. Some 1,4-bis-(alkylamino)-5-aza-ametantrone analogues have been recently synthesized by A. P. Krapcho (J. Med. Chem., (1985), 28, 1124) and were referred to possess very modest antitumor activities in "in vivo" models.

Other 2-aza-analogues, having a single side chain such as 1-[(aminoalkyl)amino]-5,8-dihydroxy-2-azaanthracene-9,10-diones were disclosed to be DNA intercalators, but inactive as antitumor agents. It is suggested that, even if the presence of two aminoalkyl chains is the best prerequisite for cytostatic activity, the presence of a nitrogen atom in the ring bearing the aminoalkyl chain dramatically changes the biological properties of the molecule (M. Croisy Delcey et al., Eur. J. Med. Chem., (1988), 23, 101).

More simple 2,3-diaza-anthracenes, devoid of the central quinone system, such as some 1,4-bis(alkylamino)-2,3-diaza-anthracenes and related 1-(alkylamino)-4-hydroxy compounds (P. Navarro et al., European J. Med. Chem., (1986), 21, 143), have been reported to have some "in vitro" antitumor activities against Hela cells, but they are also devoid of any cytostatic activity when tested in "in vivo" models, so confirming previous statements.

Until now, no examples of 2,3-diaza-anthracenediones are known at all, to further corroborate these findings.

Since 5-aza-anthracenediones are also poor cytostatic agents, nothing is known about structure-activity relationships and best mutual positions between the aza substitution and side chains. On the contrary, the available knowledge seems to suggest that the substitution of one or more C atoms of the two phenyl rings of the anthracene-9,10-dione system is detrimental for cytostatic activities.

The present invention discloses novel 2,3-diaza-anthracenedione analogues related to ametantrone provided with 1,4-(aminoalkyl) chains, both symmetrical and unsymmetrical, characterized by the presence of two nitrogen atoms in the ring bearing the aminoalkyl chains and by pronounced cytostatic activities.

The compounds of the invention may be represented by the following formula (I):

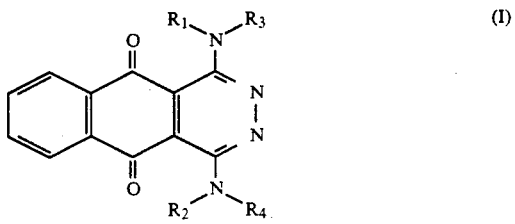

wherein:

$R_1$ and $R_2$ that can be the same or different, are hydrogen or $Ra-CO-$;

$R_3$ and $R_4$, that can be the same or different, are hydrogen, straight or branched $(C_1-C_{10})$-alkyl, a straight or branched $(C_2-C_{10})$-alkyl substituted with, at least, one substituent selected from the group consisting of $Rc-O-$, $-CHO$, $-CO-$, $-CO_2(C_1-C_4)$alkyl, $-CH[-O-(C_1-C_4)$-alkyl$]_2$, ethylenedioxyketale;

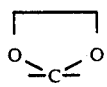

$-N(Rd,Re)$, phenyl, aromatic or not aromatic 5- or 6-membered heterocyclic ring, containing at least one heteroatom selected from the group consisting of N, O and $-N(Rb)-$, being the above mentioned $(C_2-C_{10})$-alkyl chain optionally interrupted by one or more O atoms or by $-N(Rb)-$, $-CH=CH-$ (cis or trans) or $-C\equiv C-$ groups; Ra is hydrogen, phenyl, $(C_7-C_{10})$-aralkyl, straight or branched $(C_1-C_6)$-alkyl optionally substituted by $Rf-O-$, $Rd(Re)N-(CH_2)_n-$ or by one or more halogen atoms; Rb is hydrogen, phenyl, $(C_7-C_{10})$-aralkyl, $(C_1-C_{10})$alkyl, a substituted straight or branched $(C_2-C_{10})$alkyl with at least one substituent selected from the group consisting of $Rc-O-$, $-N(Rd)Re$, phenyl, aromatic or not aromatic 5- or 6-membered heterocyclic ring containing at least one heteroatom selected from the group of N, O, $-N(Rb)-$, $Ra-CO-$, being Ra as above defined;

Rc is hydrogen, straight or branched $(C_1-C_{10})$alkyl, benzyl, 4-methoxy-benzyl and $Ra-CO-$ being Ra as above defined;

Rd and Re, that are the same or different, are selected from the group consisting of hydrogen, straight or branched $(C_1-C_{10})$-alkyl optionally substituted by branched $(C_1-C_{10})$-alkyl optionally substituted by phenyl, a 5- or 6-membered heterocyclic ring as above defined or Ra-CO; or Rd and Re, taken together with the N atom, form a 5- or 6-membered aromatic or not aromatic heterocyclic ring containing one or more N or O atoms;

Rf is benzyl, 4-methoxy-benzyl, straight or branched $(C_1-C_4)$-alkyl optionally substituted by one or more halogen atoms;

n is an integer from 1 to 6; and their salts with pharmaceutically acceptable acids.

In the compounds of formula (I), the terms such as phenyl and 5- or 6-membered heterocyclic ring refer to phenyl or a 5- or 6-membered heterocyclic rings which are optionally substituted by $(C_1-C_4)$-alkyl, $(C_1-C_4)$-polyhaloalkyl, halogen, nitro, amino, $(C_1-C_6)$-acylamino, $(C_1-C_4)$-alkylamino, $(C_1-C_4)$-alkyl-$(C_1-C_6)$-acylamino, di$(C_1-C_6)$-alkylamino, hydroxy, $(C_1-C_6)$-acyloxy, $(C_1-C_6)$-alkoxy.

Included within the scope of the present invention are the tautomeric forms, the racemic and diastereoisomeric mixtures of the compounds of formula (I) as well as the single enantiomers and diastereoisomers thereof.

Included in the scope of the present invention are also the non-toxic salts of the compounds of formula (I) with non-toxic acids, both inorganic, such as hydrochloric, hydrobromic, sulphuric, phosphoric, pyrophosphoric acids and organic, such as acetic, propionic, citric, benzoic, lactic, maleic, malic, fumaric, succinic, tartaric, glutamic, aspartic, gluconic, ascorbic acids and the like.

When in the compounds of formula (I) one of $R_3$ and $R_4$ is a straight or branched $(C_2-C_{10})$-alkyl optionally interrupted by one or more heteroatoms of O or N, at least two carbon atoms are preferably interposed between these heteroatoms.

Preferred examples of straight or branched $(C_1-C_6)$-alkyl substituted by one or more halogen atoms are trifluoromethyl, mono-, di- or trichloromethyl, 1-chloro- or 1,1-dichloro ethyl, 2,3-dichloropropyl.

Preferred examples of an aromatic or not aromatic 5- or 6-membered heterocyclic ring containing at least one oxygen or nitrogen are: 1-imidazolyl, 1-pyrrolyl, 1-tetrahydropyrrolyl, α-, β- or γ-pyridyl, 1-pyrazolyl, 2-pyrimidinyl, 1-aziridinyl, N-morpholinyl, 1-piperidinyl, 1-piperazinyl, 1-(4-methyl)piperazinyl, 1-(4-benzyl)-piperazinyl and more generally a 4-Rb-substituted piperazine, being Rb as above defined, 2-furanyl, 2-tetrahydrofuranyl, 2-(1,4-dioxanyl), 2-(1,3-dioxolanyl), 3-(tetrahydro-1,3-oxazolyl), 3-(tetr 2,2-dimethyl-1,3-oxazolyl) and 3-(tetrahydro-2-oxo-1,3-oxazolyl).

Preferred examples of optionally substituted straight or branched $(C_7-C_{10})$-aralkyl are benzyl, 4-methoxy-benzyl, cinnamyl and 4-methoxy-cinnamyl, being the cinnamyl residue a group of formula: $(trans)C_6H_5CH=CH-CH_2-$.

Specific examples of the preferred compounds of the invention are:

1,4-bis[N-(3-hydroxypropyl)amino]-2,3-diaza-anthracene-9,10-dione;

1,4-bis[N-(3-acetoxypropyl)-N-(acetyl)amino]-2,3-diaza-anthracene-9,10-dione;

1,4-bis[N-(3-acetoxypropyl)amino]-2,3-diaza-anthracene-9,10-dione;

1-[N-(3-acetoxypropyl)-N-(acetyl)amino]-4-[N-(3-acetoxypropyl)amino]-2,3-diaza-anthracene-9,10-dione;

4-amino-1-[N-(3-hydroxypropyl)amino]-2,3-diaza-anthracene-9,10-dione;

4-amino-1-[N-(3-acetoxypropyl)-N-(acetyl)amino]-2,3-diaza-anthracene-9,10-dione;

4-amino-1-[N-(3-hydroxypropyl)-N-(acetyl)amino]-2,3-diaza-anthracene-9,10-dione;

1-[N-(3-hydroxypropyl)-N-(acetyl)amino]-4-[N-(3-hydroxypropyl)amino]-2,3-diaza-anthracene-9,10-dione;

1,4-bis[N-(2-dimethylaminoethyl)amino]-2,3-diaza-anthracene-9,10-dione;

1-[N-(2-dimethylaminoethyl)-N-(acetyl)amino]-4-[N-(2-dimethylaminoethyl)amino]-2,3-diaza-anthracene-9,10-dione;

4-amino-1-[N-(2-dimethylaminoethyl)amino]-2,3-diaza-anthracene-9,10-dione;

4-amino-1-[N-(2-dimethylaminoethyl)-N-(acetyl)amino]2,3-diaza-anthracene-9,10-dione;

1,4-bis[N-(2-(2-hydroxyethylamino)ethyl)amino]-2,3-diaza-anthracene-9,10-dione;

N,N',N'',N'''-tetraacetyl-1,4-bis[N-(2-(2-acetoxyethylamino)ethyl)amino]-2,3-diaza-anthracene-9,10-dione;

4-amino-1-[N-(2-(2-hydroxyethylamino)ethyl)amino]2,3-diaza-anthracene-9,10-dione;

1,4-bis[N-(3-dimethylaminopropyl)amino]-2,3-diaza-anthracene-9,10-dione;

4-amino-1-[N-(3-dimethylaminopropyl)amino]-2,3-diaza-anthracene-9,10-dione.

The compounds of the invention can be prepared in a multi-step process comprising the oxidation of a compound of formula (II):

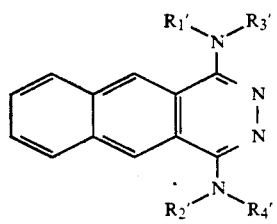

(II)

in which $R_1'$, $R_2'$, $R_3'$ and $R_4'$ are $R_1$, $R_2$, $R_3$ and $R_4$ as defined for formula I or a group or atom convertible to $R_1$, $R_2$, $R_3$ and $R_4$ to give a compound of formula Ia

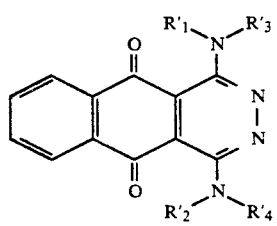

(Ia)

and then optionally performing one or more of the following steps:

a) where $R_1'$, $R_2'$, $R_3'$, $R_4'$ are other than $R_1$, $R_2$, $R_3$, $R_4$, converting $R_1'$, $R_2'$, $R_3'$ or $R_4'$ to $R_1$, $R_2$, $R_3$ or $R_4$ to obtain a compound of formula I;

b) where $R_1'$, $R_2'$, $R_3'$ and $R_4'$ are $R_1$, $R_2$, $R_3$ and $R_4$, converting one $R_1$, $R_2$, $R_3$ or $R_4$ to another $R_1$, $R_2$, $R_3$ or $R_4$ to obtain a compound of formula I;

c) forming a salt and/or solvate of the obtained compound of formula I or separating the isomers thereof.

In the optional steps of the above described process, when only one or a few substituents are specifically described for a compound, it must be understood that the other substituents have all the other meanings previously shown for a compound of formula (I).

Suitable oxidizing agents for the transformation of a compound of formula (II) into a compound of formula (Ia) are chromic anhydride and/or salts of chromic and bichromic acid with alkali or alkaline-earth metals as, for example, sodium chromate, potassium, magnesium and sodium bichromate. In order to obtain a compound of general formula (Ia), the oxidation of a compound (II) requires at least the use of a molar excess of the oxidizing agent; the reaction is carried out in a solvent such as acetic acid, propionic acid, trifluoroacetic acid, methanesulphonic acid, water and their mixtures, in the presence or not of sulphuric acid, working at a temperature ranging from 20° C. to the reflux temperature of the mixture, for a suitable reaction time.

The use of from 5 to 10 molar equivalents of a hexavalent chromium compound in aqueous acetic acid is preferred, at a temperature of 40°-60° C., for about 4 hours.

The optional addition of sulphuric acid and/or methanesulphonic acid to the reaction mixture may be particularly preferred when it is desired to obtain unsymmetrical 1,4-bis(aminosubstituted) compounds of formula (Ia) starting from the symmetrical 1,4bis-(aminosubstituted) compounds of formula (II). In fact, in the presence of variable amounts of the above mentioned acids, oxidation of the central phenyl ring to quinone is coupled also with some oxidative cleavage of one of the two 1,4-bis (aminoalkyl)-side chains of a compound of formula (II). The selective oxidative cleavage of one of these chains may be preferably performed starting from compounds of formula (II) wherein $R_2'$ is hydrogen by reaction for example in aqueous acetic acid in the presence of an excess from 15 to 20 molar equivalents of chromium trioxide, gradually added. The reaction is complete in about 6-8 hours at about 55° C.

The optional removal of the protective groups of (primary and secondary) amino and hydroxy groups present in the compounds of formula (Ia) may be performed using well known methods.

The hydrolysis of ester (for example acetate), and of amide (for example acetamido) groups present in a compound of formula (Ia), can be suitably performed with inorganic bases such as lithium, sodium or potassium hydroxide, bicarbonate and or carbonate in water, $(C_1-C_4)$-alcohols or mixtures thereof. The reaction is performed at a temperature from 0° C. to the reflux temperature of the solvent but preferably at room temperature. When one or more ester or amide groups are simultaneously present in a compound of formula (Ia), their cleavage may be performed stepwise, too. The stepwise cleavage depends on the nature and the number of protective groups present and upon the choice of the base, of the temperature and of the reaction time, being the solvolysis of ester groups generally preferred to that of amide groups. If desired, the hydrolysis may be performed using aqueous mineral acids, such as hydrochloric, hydrobromic, hydroiodic, sulphuric and phosphoric acid instead of the above described bases. Also in this case, when more ester and amide groups are simultaneously present, the choice of the acid, of the temperature and of the reaction time affects the number and the type of protective groups that can optionally be removed.

Protective groups such as benzyloxycarbonates and benzyloxycarbamates optionally present in the compounds of formula (I) may be reductively removed. In particular, 2,2,2-trihaloethylcarbonates may be reductively removed with zinc dust or with the Cu-Zn alloy both in acetic acid at room temperature or in refluxing methanol.

The compounds of formula (II) are not known, but they can be prepared by a process comprising:

a) the reaction of 1,4-dichloro-2,3-diaza-anthracene of formula (III):

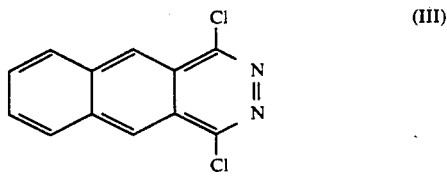

with a molar excess of an amine of formula (IV):

wherein:

P is a $R_3$ or $R_4$ group except for hydrogen, to give a compound of formula (V):

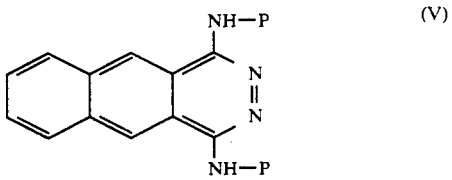

wherein P is as above defined; b) the reaction of a compound of formula (V) with an activated form of a carboxylic acid of formula (VI) $Ra'$—$CO_2H$ ($Ra'$ is Ra or is a group convertible to Ra) to give the mono or bis amides of formula (II).

The synthesis of 1,4-dichloro-2,3-diaza-anthracene (III) and its use in the preparation of some 1,4-bis (alkylamino)-2,3-diaza-anthracenes of formula (V) has been described by P. Navarro et al (above cited).

The amines of formula P—$NH_2$ are known, and some of them are commercially available. The acylation of a 1,4-bis(alkylamino)-2,3-diaza-anthracene of formula (V) to give the related 1,4-bis amide of formula (II) by reaction for example with an activated form of an acid of formula (VI), such as an acyl chloride or an anhydride can be carried out by the usual acylation methods known to those skilled in the art. For example the acylation may be performed by treatment of a compound of formula (V) with an excess of the above mentioned acylating reagents in a suitable solvent such as tetrahydrofuran, dioxane, 1,2-dichloroethane, benzene, toluene, dimethylformamide, formamide, pyridine, collidine and their mixtures in the presence of an inorganic base such as a bicarbonate or carbonate of an alkali or alkaline-earth metal (Na, Li, K, Mg) or an organic base, such as trialkylamines, pyridine, 4-dimethylaminopyridine, 2,6-lutidine, at a temperature from $-20°$ C. to the reflux temperature of the solvent.

All the unprotected primary or secondary amino or the hydroxy groups present in the P substituent of the compounds of formula (V), are also simultaneously acylated.

It is preferred to use pyridine as solvent and an excess from 1.5 to 3 molar equivalents of the acylating agent for each amino or hydroxy group present in the compound of formula (V).

The mono acylation of a compound of formula (V) to give the mono amides of formula (II), ($R'_2$=H) is performed by treatment with one molar equivalent of the above mentioned acylating reagents. Preferably this monoamidation reaction is performed with an anhydride in pyridine at room temperature.

Alternatively the same monoamides of formula (II, $R'_2$=H) may be obtained by removal of an amide group from 1,4-bis amides of formula (II, $R'_2$=$Ra'CO$—) by selective hydrolysis.

A 1,4-bis amide of formula (II) may be also transformed into its related monoamide (II, $R'_2$=H) by reaction with a hydrate of an alkali or alkaline-earth metal in water, ($C_1$-$C_4$)-alkanols or their mixtures. Preferably the reaction is carried out in a 1/1 methanol/sodium hydroxide mixture and is completed after a few hours at $50°$ C.

It is obvious that in both the mono amidation reactions other amino and hydroxy groups present in the P chains may be selectively protected.

The antitumor activity of compounds of the present invention was evaluated by "in vitro" M.T.T. assay (T. Mosmann, J. Immunol. Meth. 65 : 55–63, 1983) on human tumor cell lines. M.T.T. assay was chosen according to N.C.I. screening program for new anticancer drugs (Ad hoc review committee proceedings for N.C.I. "in vitro"—"in vivo" Disease oriented Screening project. N.I.H., Bethesda, Md. Dec.8-9, 1986). The compounds of the present invention show a significantly higher cytotoxic activity than ametantrone and mitoxantrone against various human tumor cell lines. In particular the compounds of the invention 1,4-bis[N-(2-dimethylaminoethyl)amino]-2,3-diaza-anthracene-9,10-dione (1) and 1-[N-(2-dimethylaminoethyl)amino]-4-amino-2,3-diaza-anthracene9,10-dione (2) show against human colon adenocarcinoma xenograpfht an $ID_{50}$ of $1\times10^{-8}M$ and $1\times10^{-9}M$ respectively while mitoxantrone is ten and hundred times less effective $ID_{50}=1\times10^{-7}M$). Compounds (1) and (2) when tested against human melanoma xenograpfht show $ID_{50}=1\times10^{-9}M$ and $1\times10^{-10}M$ respectively while mitoxantrone has $ID_{50}=1\times10^{-9}M$ and ametantrone has $ID_{50}=2\times10^{-5}M$.

On the same human melanoma line the compounds 1,4-bis[N-(3-hydroxypropyl)amino]-2,3-diaza-anthracene-9,10-dione (3) and 1-[N-(3-hydroxypropyl)amino]-4-amino-2,3-diaza-anthracene-9,10-dione (4) show $ID_{50}=2\times10^{-9}M$ and $1\times10^{-9}M$ respectively while the compound 1,4-bis[N-(3-hydroxypropyl)amino]-2,3-diaza-anthracene shows $ID_{50}=5\times10^{-4}M$.

Furthermore the compound 1-[N-(2-(2-hydroxyethylamino)ethyl)amino]-4-amino-2,3-diaza-anthracene-9,10-dione (5) shows against human cervix epithelioid carcinoma "in vitro" $ID_{50}=3\times10^{-9}M$. Compound (5) is as active as mitoxantrone against this cell line ($ID_{50}=5\times10^{-9}M$) but definitely more active than ametantrone ($ID_{50}=5\times10^{-5}M$). Against the same human cervix epithelioid carcinoma cell line the compounds (1) and (2) show $ID_{50}$ of $1\times10^{-9}M$ and $2\times10^{-10}M$, respectively.

In "vivo" the same compounds inhibited the growth of the above mentioned human tumor lines transplanted in nude mice.

The compounds of the present invention may be used as active ingredients of therapeutic compositions to induce regression and/or palliation of cancers in mammals, when administered in amounts ranging from about 1 mg to about 0.4 g per kilogram of body weight per day. A preferred dosage regimen for optimum results would be from about 1.0 mg to about 50 mg per kilogram of body weight per day, and such dosage units are employed, so that a total of from about 70 mg to about 3.5 g of the active compound for a subject of about 70 kg of body weight are administered in a 24 hour period.

This dosage regimen may be adjusted to provide the optimum therapeutic response.

For example, several divided doses may be administered according to the requirements of the therapeutic situation. A remarkable practical advantage is that the active compound may be administered in any convenient manner, e.g. by the oral, intravenous, intramuscular or subcutaneous routes.

Also embraced within the purview of the present invention are therapeutic compositions useful for ameliorating cancer diseases in mammals containing the novel 2,3-diaza-anthracene-9,10-diones of formula (I) or the non-toxic acid addition salts thereof.

As used herein, cancer disease means blood malignancies such as leukemia, as well as other solid and non-solid malignancies such as lung carcinomas, colon carcinomas, melanocarcinomas and mammary tumors. By regression and palliation is meant arresting or retarding the growth of the tumor or the manifestation of the disease.

Solutions for intravenous injections will normally be sterile physiological solutions. Suitable dosage forms can also include oily or aqueous injectable preparations, for intramuscular or intraperitoneal injections, syrups or the like, liquid preparations and solid dosage forms such as capsules, tablets and the like.

It is recognized that certain of the substances having the formula (I) may have such an high toxicity or such a low therapeutic index so as to be unsuitable for antitumor therapy in patients. However, these parameters can be readily determined by conventional screening test, for instance with L-1210 murine leukemia cells implanted in mice or with human transplanted tumors in nude mice and these substances should naturally be avoided.

The invention is further described by the following examples.

EXAMPLE 1

A stirred suspension of 2,3-naphthalene dicarboxylic acid (55.6 g) in acetic anhydride (380 ml) is refluxed until complete solution is obtained (about 20').

After cooling to room temperature and filtration 50.1 g of naphthalene 2,3-dicarboxylic acid anhydride are obtained, m.p. 148.2°–150° C.

A 80% solution of hydrazine hydrate (70 ml) is added at room temperature to a stirred suspension of the anhydride (48 g) in glacial acetic acid (1.2 l) and the mixture is heated for 6 hours at the reflux temperature.

After cooling, dilution with water (1.2 l) and filtration, 49.1 g of 1,4-dihydroxy-2,3-diaza-anthracene are obtained, m.p. >360° C.

A suspension of this compound (48 g) in phosphorus oxychloride (480 ml) is treated with pyridine (29 ml) and heated for 2.5 hours at 100° C. After distillation of the phosphorus oxychloride excess under reduced pressure and addition of diethyl ether (200 ml) the yellow precipitate obtained is filtered and then partitioned under vigorous stirring between ice-cold water (1 l) and ethyl acetate (1 l). The crystalline solid that separates is filtered and dried under vacuum to give 43.69 g of 1,4-dichloro-2,3-diaza-anthracene, m.p. 224°–228° C.

EXAMPLE 2

Under a nitrogen atmosphere, 1,4-dichloro-2,3diazaanthracene (3.16 g) is added to dry 2-(2-aminoethylamino)ethanol (30 ml); the mixture is heated at 120° C. for 4 hours and the red solution is then cooled to room temperature and poured into 20% aqueous ammonium sulphate (100 ml).

After removal of impurities by extraction with ethyl acetate (2×25 ml), the aqueous phase is extracted with tetrahydrofuran (10×50 ml). These extracts are combined and dried over sodium sulphate. After removal of the solvent "in vacuo" the residue is dried by azeotropic distillation with absolute ethanol (150 ml; three times).

A final solution of the residue in absolute ethanol (6 ml) is cooled to −20° C. and then after 12 hours it is diluted with ethyl acetate (70 ml).

A yellow precipitate is filtered to give 2.03 g of 1,4-bis[N-(2-(2-hydroxyethylamino)ethyl)amino]-2,3-diaza-anthracene, m.p. 129°–131° C.

EXAMPLE 3

A mixture of 1,4-dichloro-2,3-diaza-anthracene (4.84 g) and dry 1-amino-3-propanol (48 ml) is heated at 130° C. for 24 hours in an autoclave. After cooling to room temperature and dilution of the reaction mixture with a solution of potassium carbonate (96 g) in water (240 ml) a crystalline solid separates which is filtered and recrystallized from aqueous ethanol to give 6.09 g of 1,4-bis[N-(3-hydroxypropyl)amino]-2,3-diaza-anthracene, m.p. 225°–228° C.

EXAMPLE 4

Following the procedures described in the examples 2 and 3, the following compounds are prepared by reaction of 1,4-dichloro-2,3-diaza-anthracene with the properly selected amines:

1,4-bis[N-(2-dimethylaminoethyl)amino]-2,3-diaza-anthracene, m.p. 150°–154° C.;

1,4-bis[N-(2,2-dimethoxyethyl)amino]-2,3-diaza-anthracene, m.p. 176°–178° C.;

1,4-bis[N-(3-dimethylaminopropyl)amino]-2,3-diaza-anthracene;

1,4-bis[N-(2-(4'-methylpiperazin-1'-yl)ethyl)amino]2,3-diaza-anthracene;

1,4-bis[N-(2-(4'-morpholinyl)ethyl)amino]-2,3-diaza-anthracene;

1,4-bis[N-(2-(2-dimethylaminoethylamino)ethyl)amino]-2,3-diaza-anthracene;

1,4-bis[N-(2-acetylaminoethyl)amino]-2,3-diaza-anthracene;

1,4-bis[N-(2-(1'-aziridinyl)ethyl)amino]-2,3-diaza-anthracene;

1,4-bis[N-(2-(2-benzyloxyethoxy)ethyl)amino]-2,3-diaza-anthracene;

1,4-bis[N-(2-(1'-piperidinyl)ethyl)amino]-2,3-diaza-anthracene;

1,4-bis[N-(2-diethylaminoethyl)amino]-2,3-diaza-anthracene.

EXAMPLE 5

Acetic anhydride (13 ml) is added to a stirred suspension of 1,4-bis[N-(2-(2-hydroxyethylamino)ethyl) amino]-2,3-diaza-anthracene (3.03 g) in dry pyridine (15 ml) and the solution obtained is heated at 85° C. for 3.5 hours in the dark.

After distillation at reduced pressure of the excess of pyridine and acetic anhydride, the residue is taken up in methylene chloride (100 ml) and the organic solution is washed with 5% sodium bicarbonate (4×60 ml).

After reextraction of the aqueous layers with dichloromethane (50 ml) the combined organic phases are washed with brine, dried and the solvent removed at reduced pressure.

The residue is purified by column chromatography (SiO$_2$; eluent dichloromethane/methanol 20/1) to give 4.02 g of N,N',N'',N'''-tetraacetyl-1,4-bis[N-(2-(2-acetoxyethylamino)ethyl)amino]-2,3-diaza-anthracene as a light yellow foam; $^1$H-N.M.R. (CDCl$_3$) : δ 1.92, 2.01, 2,08, and 2.21, 4 s, 18 H; δ 3.35–4.05, m, 10 H; δ 4.15, m, δ 4 29, m and δ 4.50÷4.75, m, 6 H; δ 7.81, m, 2 H; δ 8.22, m, 2 H; δ 8.60, m, 2 H.

I.R. (KBr) : 1741, 1673, 1643 cm$^{-1}$.

EXAMPLE 6

Under a nitrogen atmosphere trifluoroacetic anhydride (4.23 ml) is slowly added to a stirred, cooled (−20° C.) solution of 1,4-bis[N-(2-(2-benzyloxyethoxy)ethyl) amino]-2,3-diaza-anthracene (2.80 g) in pyridine (20 ml).

After 3 hours at −20° C. and 12 hours at room temperature, the solvent is distilled at reduced pressure and the residue is purified by column chromatography (SiO$_2$; eluent ethyl acetate/triethylamine 20/0.1) to give 2.20 g of 1,4-bis[N-(2-benzyloxyethoxy)ethyl)-N-(trifluoroacetyl)amino]-2,3-diaza-anthracene.

EXAMPLE 7

Using in the procedures described in the examples 5 and 6 the properly selected acylating agents, the following compounds are prepared:

1,4-bis[N-(3-acetoxypropyl)-N-(acetyl)amino]-2,3-diaza-anthracene, m.p. 157°–158° C.;

1,4-bis[N-(2,2-dimethoxyethyl)-N-(acetyl)amino]-2,3-diaza-anthracene, m.p. 145°–146° C.;

1,4-bis[N-(2-dimethylaminoethyl)-N-(acetyl)amino]2,3-diaza-anthracene;

$^1$H N.M.R. (CDCl$_3$) : δ 1.88, s, 6 H; δ 2.12, s, 12 H; δ 2.61, t, 4 H; δ 4.13 and δ 4.29, 2 m, 4 H; δ 7.75, m, 2 H; δ 8.20, m, 2 H; δ 8.75, s, 2 H;

1,4-bis[N-(2-(4'-methylpiperazin-1'-yl)ethyl))-N(trifluoroacetyl)amino]-2,3-diaza-anthracene;

1,4-bis[N-(2-acetylaminoethyl)-N-(acetyl)amino]2,3-diaza-anthracene;

1,4-bis[N-(3-dimethylaminopropyl)-N-(trifluoroacetyl)amino]-2,3-diaza-anthracene;

1,4-bis[N-(2-(1'-aziridinyl)ethyl)-N-(trifluoroacetyl)amino]-2,3-diaza-anthracene;

N,N',N'',N'''-tetraacetyl-1,4-bis[N-(2-(2-dimethylaminoethylamino)ethyl)amino]-2,3-diaza-anthracene;

1,4-bis[N-(2-morpholinoethyl)-N-(acetyl)amino]-2,3-diaza-anthracene;

N,N'-bis-(3-diethylaminopropionyl)-1,4-bis[N-(2-dimethylaminoethyl)amino]-2,3-diaza-anthracene;

1,4-bis[N-(2-piperidinylethyl)-N-(acetyl)amino]-2,3-diaza-anthracene;

1,4-bis[N-(2-diethylaminoethyl)-N-(acetyl)amino]-2,3-diaza-anthracene.

EXAMPLE 8

A solution of 1,4-bis[N-(3-dimethylaminopropyl)amino]-2,3-diaza-anthracene (0.76 g) in pyridine (0.6 ml) and acetic anhydride (94 ml) is left at room temperature for 15 hours. After distillation of the solvent at reduced pressure the residue is dissolved in ethyl acetate (20 ml) and the organic solution is washed with 5% sodium bicarbonate (2×15 ml) and with brine (5 ml). Drying over sodium sulphate and removal of the solvent at reduced pressure gives 0.57 g of 1-[N-(3-dimethylaminopropyl)-N-(acetyl)amino]-4-[N-(3-dimethylaminopropyl)amino]-2,3-diaza-anthracene.

EXAMPLE 9

A solution of 1,4-bis[N-(2-dimethylaminoethyl)-N-(acetyl)amino]-2,3-diaza-anthracene (0.83 g) in methanol and 20% sodium hydroxide (0.85 ml) is heated at 50° C. for 3 hours and then poured into brine (8.5 ml).

After extraction with ethyl acetate (4×20 ml) the combined organic phases are dried over sodium sulphate and the solvent removed at reduced pressure to give 0.48 g of 1-[N-(2-dimethylaminoethyl)-N-(acetyl)amino]-4-[N-(2-dimethylaminoethyl)amino]-2,3-diaza-anthracene; $^1$H-N.M.R. (CDCl$_3$) : δ 1.85, s, 3 H; δ 2,17 and δ 2.36, 2 s, 12 H; δ 2.60, m, 2 H; δ 2.75, m, 2 H; δ 3.73 and δ 4.29, 2 m, 2 H; δ 6.50, br s, 1 H; δ 7.69, m, 2 H; δ 8.15, m, 2 H; δ 8.45, s, 1 H; δ 8.51, s, 1 H.

EXAMPLE 10

Using the procedures described in the examples 8 and 9 the following compounds are prepared:

1-[N-(2-morpholinoethyl)-N-(acetyl)amino]-4-[N-(2-morpholinoethyl)amino]-2,3-diaza-anthracene;

1-[N-(2-(4'-methylpiperazin-1'-yl)ethyl)-N-(acetyl) amino]-4-[N-(2-(4'-methylpiperazin-1'-yl)ethyl)amino]2,3-diaza-anthracene.

EXAMPLE 11

A solution of chromium trioxide (3.31 g) in water (2.8 ml) and acetic acid (22 ml) is added during 45' to a stirred solution of N,N',N'',N'''-tetraacetyl-1,4bis[N-(2-(2-acetoxyethylamino)ethyl)amino]-2,3-diaza-anthracene (3.82 g) in acetic acid (33 ml).

After 3 hours at 60° C., the dark solution is cooled, treated with isopropanol (8 ml), poured into 5% sodium bicarbonate (600 ml), and extracted with chloroform (3×200 ml).

The combined organic layers are washed with water (2×100 ml), 5% ice-cold sodium bicarbonate (3×100 ml) and then with brine (100 ml).

After drying over sodium sulphate and removal of the solvent at reduced pressure the residue obtained is purified by column chromatography (SiO$_2$).

Elution with ethyl acetate followed by ethyl acetate/methanol/triethylamine 16/2/0.2 removes some less polar materials. Further elution with ethyl acetate/methanol/triethylamine 16/2/0.2 gives 1.34 g of N,N',N'',N'''-tetraacetyl-1,4-bis[N-(2-(2-acetoxyethylamino)ethyl)amino]-2,3-diaza-anthracene-9,10-dione as an orange foam;

$^1$H-N.M.R. (CDCl$_3$) : δ 1.80, 1.95, 2.05, 2.16, 2.19 and 2.51, br, s, 18 H; δ 3.62, 4.20 and 4.58, br, m, 16 H; δ 7.86, m, 2 H; δ 8.13, m, 2 H.

A solution of this compound (0.43 g) in 37% HCl (5.5 ml) is heated at 85° C. for 6 hours. After cooling to 0° C.

the solution is made alkaline with 20% sodium hydroxide and extracted with chloroform (4×70 ml).

The combined organic layers are washed with brine, dried over sodium sulphate and the solvent distilled under reduced pressure. The residue is recrystallized from absolute ethanol to give 0.14 g of blue-black crystals of 1,4-bis[N-(2-(2-hydroxyethylamino)ethyl)amino]-2,3-diaza-anthracene-9,10-dione, m.p. 116°–120° C.

EXAMPLE 12

96% sulphuric acid (0.47 ml) is added at room temperature to a stirred solution of 1,4-bis[N-(2-dimethylaminoethyl)-N-(acetyl)amino]-2,3-diaza-anthracene (0.73 g) in acetic acid (9.5 ml). A solution of chromium trioxide (1.01 g) in water (0.7 ml) and acetic acid (7.0 ml) is then added during 20'. After heating at 60° C. for 4 hours the reaction mixture is cooled, treated with isopropanol (0.5 ml), diluted with brine (10 ml) and made alkaline with 20% sodium hydroxide at 0° C.

The precipitate obtained is filtered and washed thoroughly with ethyl acetate (60 ml). The aqueous filtrate is extracted with ethyl acetate (3×4 ml) and the combined organic solutions are dried over sodium sulphate. Removal of the solvent at reduced pressure gives 0.30 g of a mixture of 1-[N-(2-dimethylaminoethyl)-N-(acetyl)amino]-4-[N-(2-dimethylaminoethyl)amino]-2,3-diaza-anthracene-9,10-dione and 4-amino-1-[N-(2-dimethylaminoethyl)-N-(acetyl)amino]-2,3-diaza-anthracene-9,10-dione. A solution of this mixture in water (0.7 ml) and 37% HCl (1.3 ml) is heated at 90° C. for 8 hours. After cooling, the reaction mixture is diluted with water (3 ml) and alkalinized (pH 9) with 20% sodium hydroxide to give a blue precipitate which is filtered, dried and purified by column chromatography (SiO2). By elution with methylene chloride ride / methanol 16.5/3.5, 36 mg of crystalline blue 4-amino-1-[N-(2-dimethylaminoethyl)amino]-2,3-diaza-anthracene-9,10-dione, m.p. 181°–184° C. are obtained.

Further elution with methylene chloride / methanol / triethylamine 18/2/0.2 gives 0.14 g of crystalline blue 1,4-bis[N-(2-dimethylaminoethyl)amino]-2,3-diaza-anthracene-9,10-dione, m.p. 195°–197° C. (from methylene chloride / methanol).

EXAMPLE 13

A solution of chromium trioxide (5.44 g) in water (3.5 ml) and acetic acid (31 ml) is added to a well stirred solution of 1,4-bis[N-(3-acetoxypropyl)-N-(acetyl) amino]-2,3-diaza-anthracene (5.40 g) in acetic acid (31 ml), at such a rate that the temperature does not rise over 35° C. The addition requires about one hour. The mixture is then heated at 55° C. for one hour. After cooling to room temperature, the excess of chromium trioxide is destroyed with isopropanol (8 ml) and the reaction mixture is poured into water. After neutralization with sodium bicarbonate the aqueous phase is extracted with chloroform (3×100 ml). The combined organic layers are evaporated to dryness under reduced pressure; the residual mixture of 1,4-bis[N-(3-acetoxypropyl)-N-(acetyl)amino]-2,3-diaza-anthracene9,10-dione and of 4-amino-1-[N-(3-acetoxypropyl)-N-(acetyl)amino]-2,3-diaza-anthracene-9,10-dione (3,99 g) is dissolved in methanol (30 ml) and treated with 1N sodium hydroxide (16 ml) at room temperature for 45'. After dilution with a saturated solution of NaH2PO4 (100 ml) and water (200 ml) the mixture is extracted with methylene chloride (3×100 ml). Removal of the solvent at reduced pressure affords a residue which is purified by silica gel column chromatography.

By elution with ethyl acetate / n-hexane / methanol 20/5/1, 0.42 g of crystalline brown 4-amino-1[N-(3-hydroxypropyl)-N-(acetyl)amino]-2,3-diaza-anthracene-9,10-dione are obtained, m.p. 201°–203° C. (from isopropanol). By further elution with ethyl acetate / methanol 92/8, 2.04 g of 1-[N-(3-hydroxypropyl)-N-(acetyl)amino]-4-[N-(3-hydroxypropyl)amino]-2,3-diaza-anthracene-9,10-dione are obtained as a purple solid, m.p. 67°–70° C. (from diethyl ether).

EXAMPLE 14

A solution of chromium trioxide (0.62 g) in water (0.53 ml) and acetic acid (3.2 ml) is added in about 15' to a well-stirred solution of 1-[N-(2-dimethylaminoethyl)-N-(acetyl)amino]-4-[N-(2-dimethylaminoethyl) amino]-2,3-diaza-anthracene (0.20 g) in acetic acid (1.5 ml). The reaction mixture is heated at 55° C. for 6.5 hours, being at intervals of about 2 hours two more portions of chromium trioxide (0.16 g) dissolved in water (0.15 ml) and acetic acid (0.8 ml) added to the reaction mixture. A last portion of chromium trioxide (74 mg) dissolved in water (0.15 ml) and acetic acid (0.4 ml) is added at the sixth hour.

After cooling to room temperature the excess of chromium trioxide is destroyed with isopropanol (0.5 ml); the mixture is left at room temperature overnight, then it is diluted with water (15 ml), cooled and made alkaline (pH 9) with 20% sodium hydroxide.

Extraction with ethyl acetate (3×20 ml), drying of the combined organic layers and removal of the solvent at reduced pressure gives 57 mg of 4-amino-1-[N-(2-dimethylaminoethyl)-N-(acetyl)amino]-2,3-diaza-anthracene-9,10-dione as a red foam;

$^1$H - N.M.R. (CDCl$_3$) : δ 1.90, s, 3 H; δ 2.09, s, 3 H; 250, m, 3 H; δ 3.60, m, 1 H; δ 4.11, m, 1 H; δ 7.80, m, 2 H; δ 8.18, m, 2 H.

EXAMPLE 15

A compound of formula (II), prepared in accordance with the procedures of the examples 5–10, is oxidized using the procedure of the examples 11–14 to give the following compounds:

1,4-bis[N-(3-hydroxypropyl)amino]-2,3-diaza-anthracene-9,10-dione, m.p. 173°–176° C.;

4-amino-1-[N-(3-hydroxypropyl)amino]-2,3-diaza-anthracene-9,10-dione, m.p. 179°–181° C.;

1-[N-(2-dimethylaminoethyl)-N-(acetyl)amino]-4-[N-(2-dimethylaminoethyl)amino]- 2,3-diaza-anthracene9,10-dione, m.p. 119°–122° C.;

4-amino-1-[N-(2-(2-hydroxyethylamino)ethyl)amino]2,3-diaza-anthracene-9,10-dione, m.p. 155° C.;

1,4-bis[N-(3-dimethylaminopropyl)amino]-2,3-diaza-anthracene-9,10-dione, m.p. 122°–124° C.;

1,4-bis[N-(2-(4'-methylpiperazin-1'-yl)ethyl) amino]-2,3-diaza-anthracene-9,10-dione;

4-amino-1-[N-(2-(4'-morpholinyl)ethyl)amino]-2,3-diaza-anthracene-9,10-dione;

1,4-bis[N-(2-(4'-morpholinyl)ethyl)amino]-2,3-diaza-anthracene-9,10-dione;

1,4-bis[N-(2-(2-dimethylaminoethylamino)ethyl) amino]-2,3-diaza-anthracene-9,10-dione;

1,4-bis[N-(2-aminoethyl)amino]-2,3-diaza-anthracene-9,10-dione;

1,4-bis[N-(2-acetylaminoethyl)-N-(acetyl)amino]2,3-diaza-anthracene-9,10-dione;

1,4-bis[N-(2-(1'-aziridinyl)ethyl)amino]-2,3-diaza-anthracene-9,10-dione;

N,N'-bis[3-diethylaminopropionyl]-1,4-bis[N-(2-dimethylaminoethyl)amino]-2,3-diaza-anthracene-9,10-dione.

1,4-bis[N-(2-(1'-piperidinyl)ethyl)amino]-2,3-diaza-anthracene-9,10-dione, m.p. 203°-204° C.;

1,4-bis[N-(2-diethylaminoethyl)amino]-2,3-diaza-anthracene-9,10-dione, m.p. 173°-175° C.;

4-amino-1-[N-(2-(1'-piperidinyl)ethyl)amino]-2,3-diaza-anthracene-9,10-dione;

4-amino-1-[N-(2-diethylaminoethyl)amino]-2,3-diaza-anthracene-9,10-dione.

EXAMPLE 16

Anhydrous hydrochloric acid is bubbled into a cooled (0° C.) solution of 1,4-bis[N-(3-hydroxypropyl)amino]-2,3-diaza-anthracene-9,10-dione (0.27 g) in methanol/ chloroform 1/1 (26 ml).

After 15' the suspension is diluted with diethyl ether (80 ml) and the precipitate filtered under a nitrogen atmosphere to give 0.23 g of 1,4-bis[N-(3-hydroxypropyl)amino]-2,3-diaza-anthracene-9,10-dionemonohydrochloride, m.p. 186°-188° C.

EXAMPLE 17

Using in the procedure described in the example 16 the suitable compounds of formula (I), the following compounds are prepared:

4-amino-1-[N-(3-hydroxypropyl)amino]-2,3-diaza-anthracene-9,10-dione-monohydrochloride, m.p. 204°-205° C.;

1,4-bis[N-(2-dimethylaminoethyl)amino]-2,3-diaza-anthracene-9,10-dione-trihydrochloride . 1,5 H₂O, m.p. 252°-255° C.;

4-amino-1-[N-(2-dimethylaminoethyl)amino]-2,3-diaza-anthracene-9,10-dione-bishydrochloride, m.p. 219.5°-221.5° C.;

4-amino-1-[N-(2-(2-hydroxyethylamino)ethyl)amino]-2,3-diaza-anthracene-9,10-dione bishydrochloride, m.p. 202°-204° C.;

1,4-bis[N-(2-(2-hydroxyethylamino)ethyl)amino]-2,3-diaza-anthracene-9,10-dione-trihydrochloride, m.p. 210°-211° C.;

1,4-bis[N-(3-dimethylaminopropyl)amino]-2,3-diaza-anthracene-9,10-dione-trihydrochloride, m.p. 241°-243° C.

EXAMPLE 18

Acetic anhydride (4 ml) is added at room temperature to a stirred suspension of 1,4-bis[N-(3-hydroxypropyl)amino]-2,3-diaza-anthracene-9,10-dione (0.29 g) in pyridine (4 ml).

After 4 hours the precipitate is filtered, washed with diethyl ether and recrystallized from methanol to give 0.19 g of 1,4-bis[N-(3-acetoxypropyl)amino]-2,3-diaza-anthracene-9,10-dione, m.p. 142°-145° C.

EXAMPLE 19

Using in the procedure described in the example 18 the suitable compounds of formula (I), the following compounds are prepared:

1-[N-(3-acetoxypropyl)-N-(acetyl)amino]-4-[N-(3-acetoxypropyl)amino]-2,3-diaza-anthracene-9,10-dione, I.R. (CHCl₃) : 1733, 1653 cm⁻¹;

1,4-bis{N-2-[N'-(2'-dimethylaminoethyl)-N'-(acetyl)amino]ethylamino}-2,3-diaza-anthracene-9,10-dione;

1,4-bis[N-(2-acetylaminoethyl)amino]-2,3-diaza-anthracene-9,10-dione;

1,4-bis{N-2-[N'-(2'-acetoxyethyl)-N'-(acetyl) amino]ethylamino}-2,3-diaza-anthracene-9,10-dione;

¹H-N.M.R. (CDCl₃) : δ 2.01-2.18, 4 s, 12 H; δ 3.58-3.79, 2 m, 8 H; δ 3.97, m, 4 H; δ 4.18 and 4.25, 2 m, 4 H; δ 7.81, m, 2 H; δ 8.20, m, 2 H; δ 8.70, m, 2 H.

We claim:

1. A compound of the formula

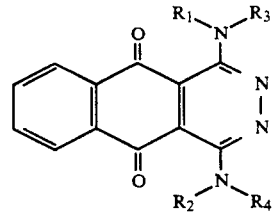

R₁ and R₂, which can be the same or different, are hydrogen or RaCO—;

R₃ and R₄, which can be the same or different, are hydrogen, straight or branched (C₁-C₁₀)-alkyl, straight or branched (C₂-C₁₀)alkyl substituted with one substituent selected from the group consisting of Rc—O—, —CH[—O—(C₁-C₄)-alkyl]₂, 1,3-dioxolan-2-yl and —N(Rd)(Re), and wherein the above mentioned (C₂-C₁₀)-alkyl chain may be optionally interrupted by one or more O atoms or by —N(Rb)—; Ra is straight or branched (C₁-C₁₀)-alkyl optionally substituted by (Rd) (Re)N—(CH₂)ₙ—or by one or more halogen atoms; Rb is hydrogen, (C₁-C₁₀)-alkyl, a substituted straight or branched (C₂-C₁₀)-alkyl substituted by one substituent selected from the group consisting of Rc—O—, —N(Rd)(Re), and Ra—CO—, Ra being defined as above; Rc is hydrogen, straight or branched (C₁-C₁₀)-alkyl, benzyl or RaCO—, Ra being defined as above; Rd and Re, which are the same or different, are selected from the group consisting of hydrogen and straight or branched (C₁-C₁₀)-alkyl optionally substituted by 4'-(C₁-C₄ alkyl)-piperazin-1-yl, morpholin-4'yl, aziridin-1'-yl, piperidin-1'-yl or Ra-CO; or Rd and Re, taken together with the N atom, form 4'-(C₁-C₄ alkyl)piperazine, morpholine, aziridine or piperidine; and n is an integer from 1 and 4; or their salts with pharmaceutically acceptable acids.

2. A compound according to claim 1 wherein R₁ is identical to R₂ and R₃ is identical to R₄.

3. A compound according to claim 1 wherein R₂ and R₄ are both hydrogen.

4. A compound according to claim 1 wherein R₁ and R₂ are hydrogen.

5. A compound according to claim 1 wherein R₁ and R₂ are acetyl groups.

6. A compound of the formula

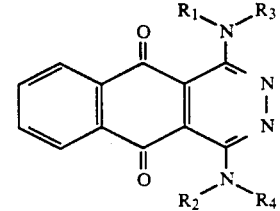

wherein:

$R_1$ and $R_2$, which can be the same or different, are hydrogen or acetyl;

$R_3$ and $R_4$, which can be the same or different, are $(C_1-C_6)$-alkyl.

7. A pharmaceutical composition having antitumor activity comprising an effective amount of a compound of any one of claims 1 and 2-and 6 in admixture with a suitable carrier.

* * * * *